US010660610B2

(12) United States Patent
Henderson et al.

(10) Patent No.: US 10,660,610 B2
(45) Date of Patent: May 26, 2020

(54) ULTRASOUND SYSTEM AND TRANSDUCER ASSEMBLIES

(71) Applicant: Edan Instruments, Inc., Shenzhen (CN)

(72) Inventors: Richard Henderson, Sunnyvale, CA (US); Sean Murphy, Sunnyvale, CA (US)

(73) Assignee: Edan Instruments, Inc., Shenzhen (CN)

( * ) Notice: Subject to any disclaimer, the term of this patent is extended or adjusted under 35 U.S.C. 154(b) by 1091 days.

(21) Appl. No.: 15/088,748

(22) Filed: Apr. 1, 2016

(65) Prior Publication Data

US 2016/0317124 A1 Nov. 3, 2016

Related U.S. Application Data

(63) Continuation of application No. 13/943,779, filed on Jul. 16, 2013, now Pat. No. 9,301,731.

(51) Int. Cl.
*A61B 8/00* (2006.01)
*H01R 13/70* (2006.01)

(52) U.S. Cl.
CPC .............. *A61B 8/4433* (2013.01); *A61B 8/44* (2013.01); *A61B 8/4405* (2013.01);
(Continued)

(58) Field of Classification Search
CPC ....... A61B 8/00; A61B 8/4433; A61B 8/4455; A61B 8/4483; A61B 8/4427; A61B 8/4405; A61B 8/4477
See application file for complete search history.

(56) References Cited

U.S. PATENT DOCUMENTS

| 5,313,596 A | 5/1994 | Swindler et al. |
|---|---|---|
| 5,846,097 A | 12/1998 | Marian, Jr. |

(Continued)

FOREIGN PATENT DOCUMENTS

| EP | 0 829 735 A2 | 3/1998 |
|---|---|---|
| EP | 2 267 482 A1 | 12/2010 |
| WO | WO 2005/053664 A2 | 6/2005 |

OTHER PUBLICATIONS

International Search Report and Written Opinion issued in related International Patent Application No. PCT/US2014/046622, completed Oct. 30, 2014.

(Continued)

*Primary Examiner* — Joel Lamprecht
(74) *Attorney, Agent, or Firm* — Gilberto M. Villacorta; Brett P. Belden; Foley & Lardner LLP

(57) ABSTRACT

An ultrasound system is disclosed. The ultrasound system includes an ultrasound device. The ultrasound device includes a housing, a control panel coupled to the housing, and a receiver assembly coupled to the housing, wherein the receiver assembly includes a first contact surface. The ultrasound system further includes a transducer assembly having an ultrasound probe and a cartridge, wherein the cartridge includes a second contact surface. The cartridge is configured to be removably received in a slot of the receiver assembly such that the cartridge is movable between a removed position, in which the transducer assembly is not connected to the ultrasound device, and an engaged position, in which the cartridge is positioned in the slot and the first contact surface is electrically coupled to the second contact surface.

15 Claims, 16 Drawing Sheets

(52) U.S. Cl.
CPC .......... *A61B 8/4411* (2013.01); *A61B 8/4427* (2013.01); *A61B 8/4444* (2013.01); *A61B 8/4455* (2013.01); *A61B 8/4477* (2013.01); *A61B 8/4483* (2013.01); *H01R 13/701* (2013.01)

(56) References Cited

U.S. PATENT DOCUMENTS

| | | |
|---|---|---|
| 5,865,650 A | 2/1999 | Marian, Jr. et al. |
| 5,971,923 A | 10/1999 | Finger |
| 6,417,857 B2 | 7/2002 | Finger et al. |
| 7,127,401 B2 | 10/2006 | Miller |
| 7,223,242 B2 | 5/2007 | He et al. |
| 7,352,570 B2 | 4/2008 | Smith et al. |
| 7,362,567 B1 | 4/2008 | Hsieh et al. |
| 7,471,301 B2 | 12/2008 | Lefevre |
| 7,527,591 B2 | 5/2009 | Haugen et al. |
| 8,002,708 B2 | 8/2011 | Shah et al. |
| 8,088,070 B2 | 1/2012 | Pelissier et al. |
| 2005/0251035 A1 | 11/2005 | Wong et al. |
| 2006/0039105 A1* | 2/2006 | Smith ...................... A61B 8/00 361/679.26 |
| 2010/0152589 A1 | 6/2010 | Asai et al. |
| 2012/0267981 A1 | 10/2012 | Morris et al. |

OTHER PUBLICATIONS

International Preliminary Report on Patentability issued in related International Patent Application No. PCT/US2014/046622, dated Jan. 19, 2016.

\* cited by examiner

ULTRASOUND SYSTEM AND TRANSDUCER ASSEMBLIES

CROSS-REFERENCE TO RELATED APPLICATIONS

This application is a continuation of U.S. patent application Ser. No. 13/943,779, titled "ULTRASOUND SYSTEM AND TRANSDUCER ASSEMBLIES," filed Jul. 16, 2013, the entire disclosure of which is incorporated herein by reference in its entirety for any and all purposes.

BACKGROUND

The present application relates to ultrasound systems. More specifically, the present application relates to an ultrasound system and transducers assemblies for the ultrasound system.

SUMMARY

One embodiment of the present disclosure relates to an ultrasound system. The ultrasound system includes an ultrasound device. The ultrasound device includes a housing, a control panel coupled to the housing, and a receiver assembly coupled to the housing, wherein the receiver assembly includes a first contact surface. The ultrasound system further includes a transducer assembly having an ultrasound probe and a cartridge, wherein the cartridge includes a second contact surface. The cartridge is configured to be removably received in a slot of the receiver assembly such that the cartridge is movable between a removed position, in which the transducer assembly is not connected to the ultrasound device, and an engaged position, in which the cartridge is positioned in the slot and the first contact surface is electrically coupled to the second contact surface.

Another embodiment of the present disclosure relates to the ultrasound system wherein the receiver assembly further includes an actuator configured to pull the cartridge from a partially inserted position to the engaged position.

Yet another embodiment of the present disclosure relates to the ultrasound system wherein the receiver assembly further includes at least one of a switch or a sensor that detects the presence of the cartridge when the cartridge is in the partially inserted position, and wherein a controller is configured to activate the actuator based on a feedback signal from the at least one of the switch or the sensor.

Another embodiment of the present disclosure relates to the ultrasound system wherein the first contact surface is movably coupled to the housing.

Yet another embodiment of the present disclosure relates to the ultrasound system wherein the first contact surface and the second contact surface each include a plurality of conductive surfaces.

Still another embodiment of the present disclosure relates to the ultrasound system wherein the plurality of conductive surfaces are bowed such that when the cartridge is in the engaged position, the bowed conductive surfaces deform providing a holding force that resists cartridge movement from the engaged position to the removed position.

Another embodiment of the present disclosure relates to the ultrasound system wherein the first contact surface and the second contact surface include a plurality of interengaging pins and recesses.

Yet another embodiment of the present disclosure relates to the ultrasound system wherein the receiver assembly further includes an actuator configured to move the first contact surface into contact with the second contact surface when the cartridge moves to the engaged position.

Still another embodiment of the present disclosure relates to the ultrasound system wherein the transducer assembly further includes a cover, wherein the cover is slidably coupled to the cartridge such that the cover is movable between a first position, in which the second contact surface is covered, and a second position, in which the second contact surface is exposed.

Another embodiment of the present disclosure relates to the ultrasound system wherein an actuator is configured to move the cover between the first position and the second position.

Yet another embodiment of the present disclosure relates to the ultrasound system wherein the receiver assembly includes a first tab and the cover includes a second tab, wherein the first tab and the second tab engage such that the cover is moved from the first position to the second position as the cartridge is moved from the removed position to the engaged position.

Still another embodiment of the present disclosure relates to the ultrasound system wherein the cartridge includes a holder configured to receive the probe.

Another embodiment of the present disclosure relates to an ultrasound device. The ultrasound device includes a housing, a control panel coupled to the housing, and a receiver assembly coupled to the housing, wherein the receiver assembly includes a slot and a first contact surface. The slot is configured to receive a cartridge of a transducer assembly. The first contact surface is configured to contact a second contact surface of the transducer assembly when the cartridge of the transducer assembly is positioned within the slot.

Yet another embodiment of the present disclosure relates to the ultrasound device further including an actuator configured to pull the cartridge from a partially inserted position to an engaged position in the slot.

Still another embodiment of the present disclosure relates to the ultrasound device further including at least one of a switch or a sensor that detects the presence of the cartridge when the cartridge is in the partially inserted position, wherein a controller is configured to activate the actuator based on a feedback signal from the at least one of the switch or the sensor.

Another embodiment of the present disclosure relates to the ultrasound device wherein the first contact surface is movably coupled to the housing.

Yet another embodiment of the present disclosure relates to the ultrasound device further including an actuator configured to move the first contact surface into contact with the second contract surface when the cartridge is inserted into the slot.

Still another embodiment of the present disclosure relates to an ultrasound transducer assembly. The ultrasound transducer assembly includes a housing, an ultrasound probe coupled to the housing via a cable, and a first contact surface coupled to the housing. The housing is configured to be received in a slot of an ultrasound device. The first contact surface is configured to contact a second contact surface of the ultrasound device when the housing is positioned within the slot such that the ultrasound probe is electrically coupled to the ultrasound device.

Another embodiment of the present disclosure relates to the ultrasound transducer assembly further including a holder configured to receive the ultrasound probe.

Yet another embodiment of the present disclosure relates to the ultrasound transducer assembly further including a cover, wherein the cover is slidably coupled to the cartridge such that the cover is movable between a first position, in which the second contact surface is covered, and a second position, in which the second contact surface is exposed.

The foregoing summary is illustrative only and is not intended to be limiting in any way. In addition to the illustrative aspects, embodiments, and features described above, further aspects, embodiments, and features ill become apparent by reference to the drawings and the following detailed description.

BRIEF DESCRIPTION OF THE DRAWINGS

The disclosure will become more fully understood from the following detailed description taken in conjunction with the accompanying drawings wherein like reference numerals refer to like elements, in which.

DETAILED DESCRIPTION

Before turning to the figures which illustrate the exemplary embodiments in detail, it should be understood that the application may be not limited to the details or methodology set forth in the description or illustrated in the figures. It should also be understood that the terminology may be for the purpose of description only, and should not be regarded as limiting.

Figure 1:
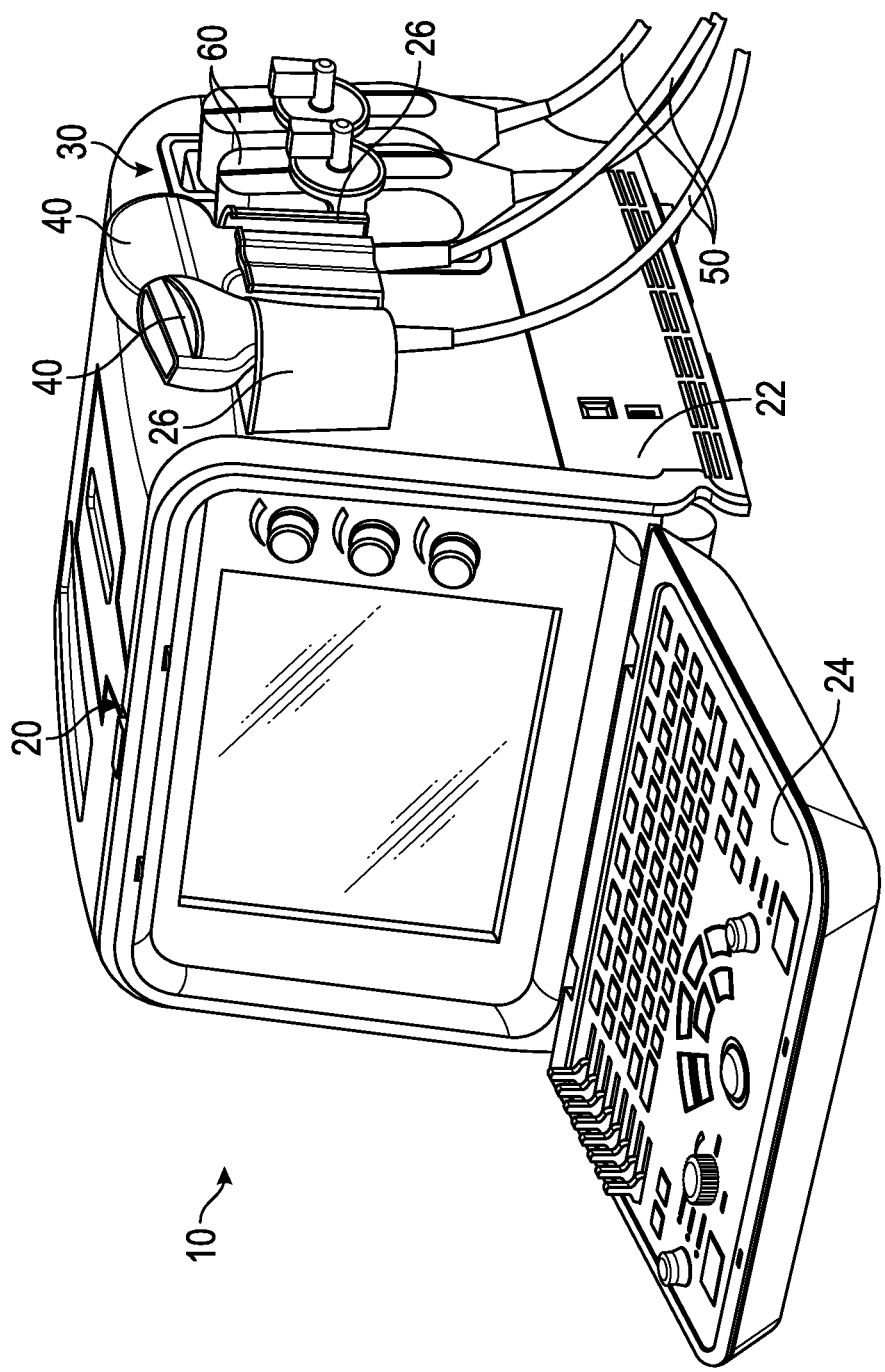
FIGS. 1-4 are elevation views of traditional ultrasound equipment.
Figure 2:
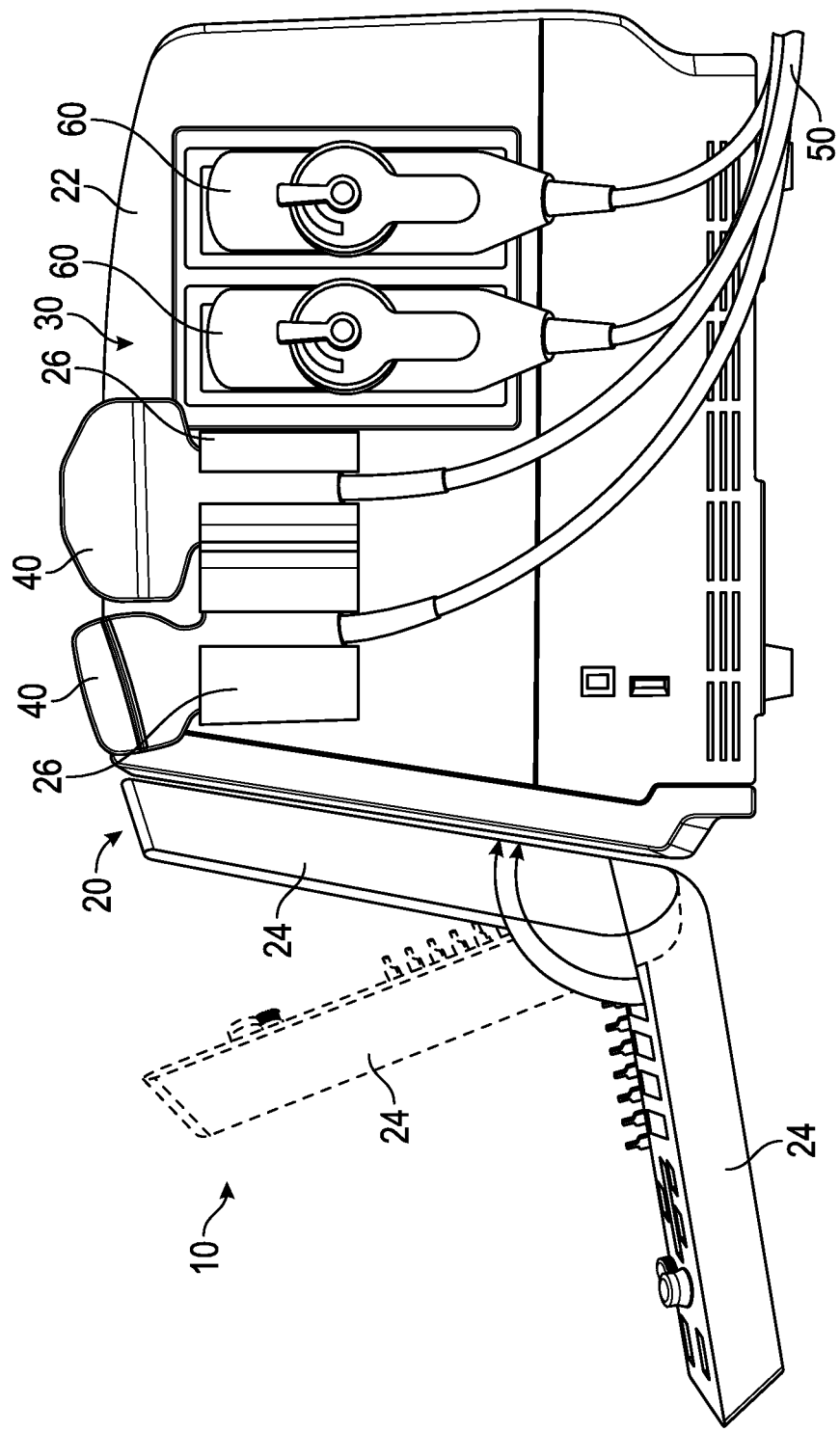

Referring to FIGS. 1-2, traditional ultrasound equipment 10 includes an ultrasound system 20 coupled to a transducer assembly 30. Ultrasound equipment 10 may be used to perform a diagnostic ultrasound examination (e.g., an abdominal, an obstetric and gynecological, a cardiac, a pediatric, a musculoskeletal, etc.). Ultrasound system 20 includes a body, shown as housing 22, a user interface, shown as control panel 24, and one or more holders, shown as brackets 26. As shown in FIG. 2, control panel 24 may be rotatably coupled to housing 22 (e.g., with a pinned connection) and moveable between a first position (e.g., an operational position) and a second position (e.g., a storage position). Transducer assembly 30 includes two transducer probes 40 that are coupled to ultrasound system 20 with cables 50 and connectors 60. A connector 60 is coupled to a first end of cable 50, and a transducer probe 40 is coupled to a second end of cable 50. As shown in FIGS. 1 and 2, cable 50 electrically couples transducer probe 40 to ultrasound system 20. While shown in FIG. 2 as having two transducer probes 40, cables 50, and connectors 60, transducer assembly 30 may have more or fewer transducer probes 40, cables 50, and connectors 60. Each transducer probe 40 transmits and receives ultrasound signals that interact with the patient during the diagnostic ultrasound examination. Transducer probes 40 may be stored within brackets 26 when not in use. A user (e.g., a sonographer, an ultrasound technologist, etc.) may remove a transducer probe 40 from a bracket 26, position transducer probe 40, and interact with control panel 24 to conduct the diagnostic ultrasound examination. Conducting the diagnostic ultrasound examination may include pressing transducer probe 40 against the patient's body or placing transducer probe 40 into the patient.

Figure 3:
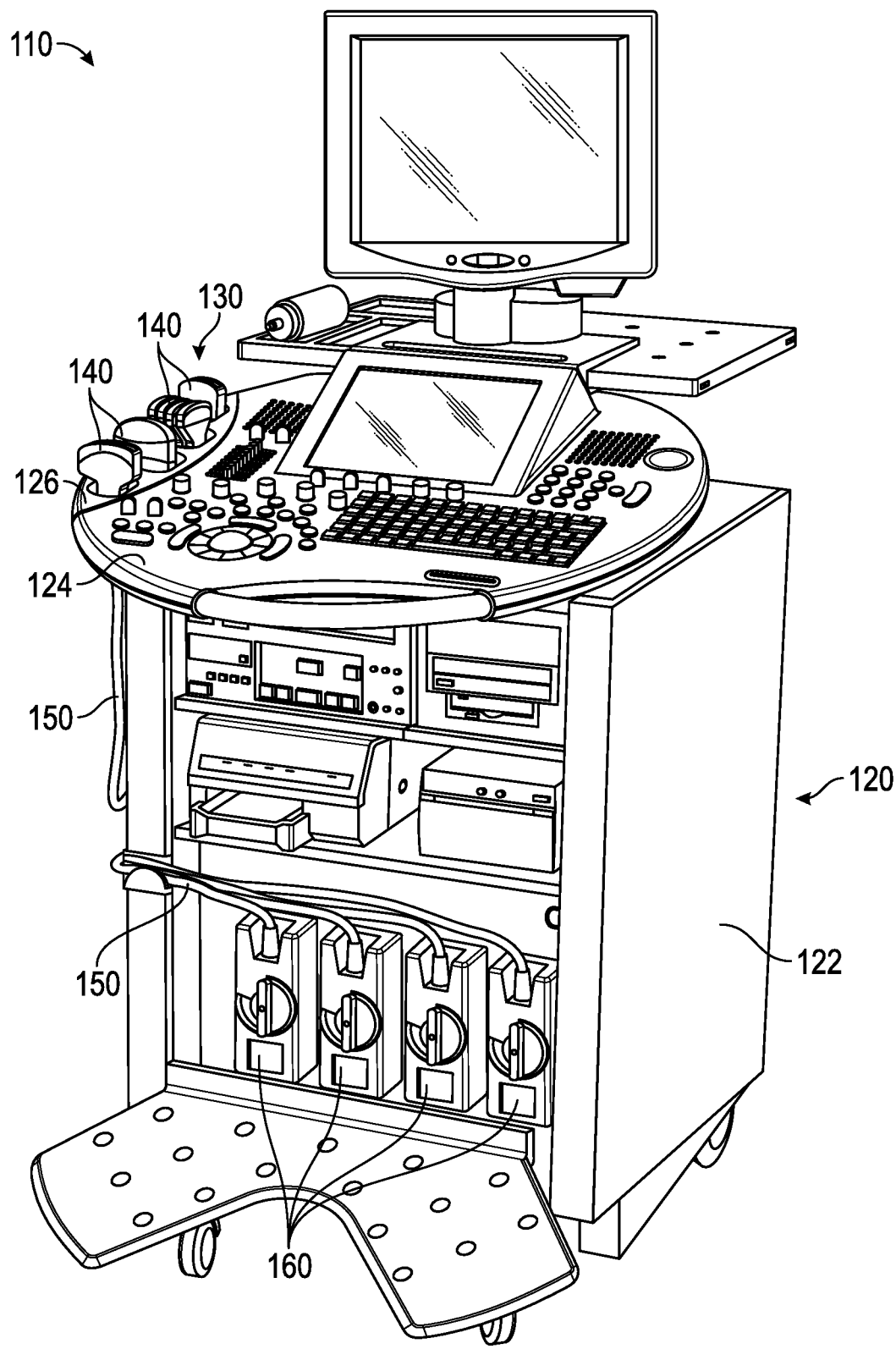
Figure 4:
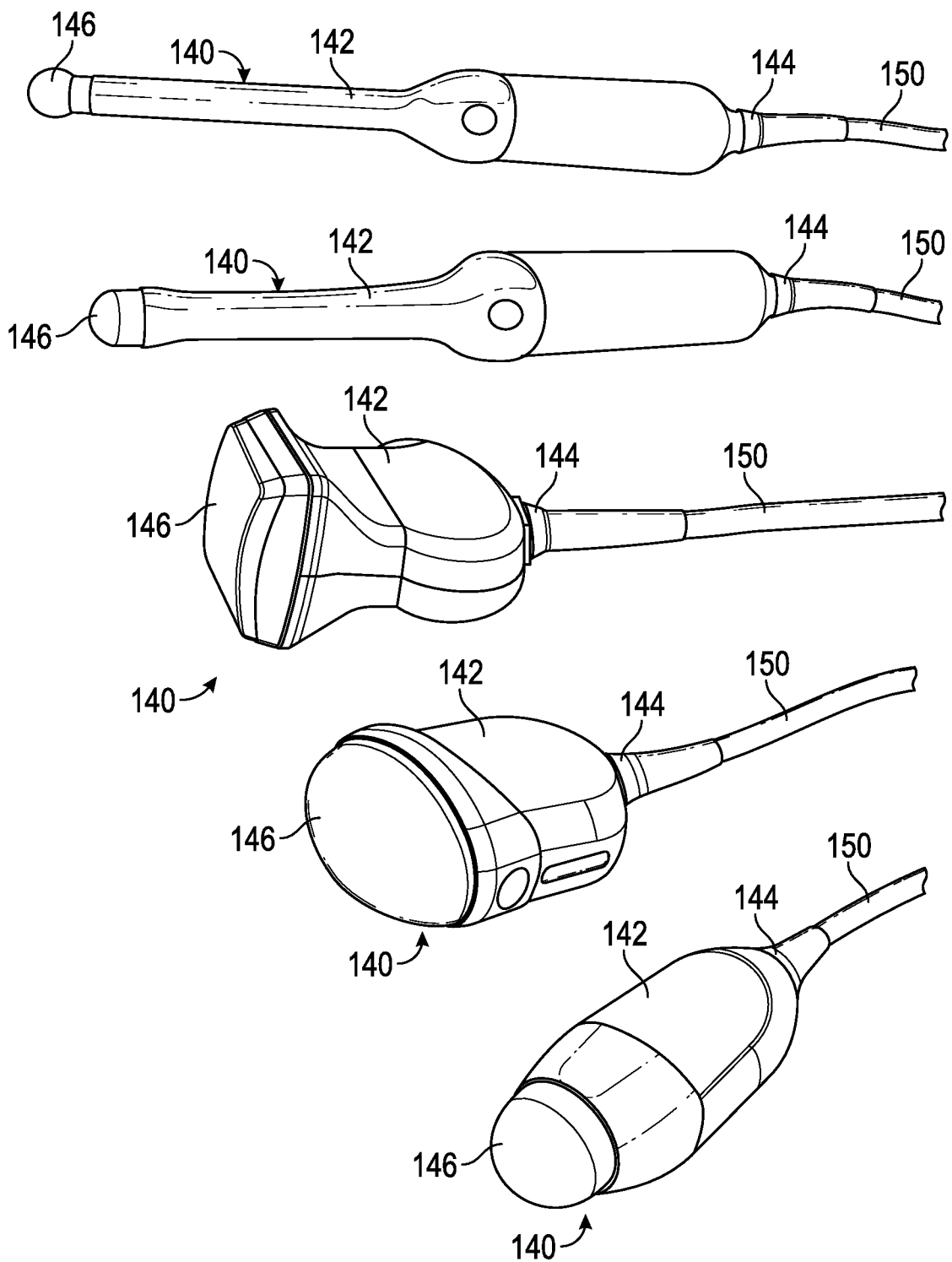

Referring next to FIGS. 3-4, traditional ultrasound equipment 110 includes an ultrasound system 120 coupled to a transducer assembly 130. Ultrasound system 120 includes a body, shown as housing 122, a user interface, shown as control panel 124, and a holder, shown as bracket 126. As shown in FIG. 3, transducer assembly 130 includes four transducer probes 140 that are coupled to ultrasound system 120 with cables 150 and connectors 160. While shown in FIG. 3 as having four transducer probes 140, cables 150, and connectors 160, transducer assembly 130 may have more or fewer transducer probes 140, cables 150, and connectors 160. Bracket 126 is coupled to housing 122 at approximately the same vertical position as control panel 124. Bracket 126 may be positioned at the perimeter of control panel 124 or in another location. As shown in FIG. 3, connectors 160 are coupled to ultrasound system 120 at a vertical position below control panel 124. By way of example, connectors 160 may be positioned near an end of housing 122 configured to interface with a floor surface.

As shown in FIG. 4, different transducer probes 140 may be used to conduct different types of diagnostic ultrasound examinations. Traditional transducer probes 140 each include a body 142 having a first end 144 and a second end 146. First end 144 of each transducer probe 140 is coupled to a cable 150. As shown in FIG. 4, first end 144 and second end 146 of each transducer probe 140 have different shapes. By way of example, second end 146 may be shaped to facilitate positioning transducer probe 140. First ends 144 of transducer probes 140 each have a different shape, as shown in FIG. 4.

Traditional transducer assembly 130 may include different transducer probes 140 such that a user may conduct the different diagnostic ultrasound examinations with a single piece of ultrasound equipment 110. Transducer probes 140 may be stored within bracket 126 when not in use. A user may remove a transducer probe 140 from bracket 126, position transducer probe 140, and interact with control panel 124 to conduct the diagnostic ultrasound examination. As shown in FIG. 3, cables 150 extend from connectors 160, across housing 122, and upwards to transducer probes 140. Use of different transducer probes 140 either sequentially or simultaneously may entangle cables 150. Cables 150 may also become engaged with the user's legs, with a hospital bed, or with still other equipment. Entangled cables 150 may increase the time and effort needed to disengage a transducer probe 140, cable 150, and connector 160 from ultrasound system 120 (e.g., to engage and utilize a different transducer probe 140). Connectors 160 may be locked into housing 122 (e.g., with a manual knob or lever) to reduce the risk that connectors 160 may disengage ultrasound system 120 during a diagnostic ultrasound examination.

Figure 5:
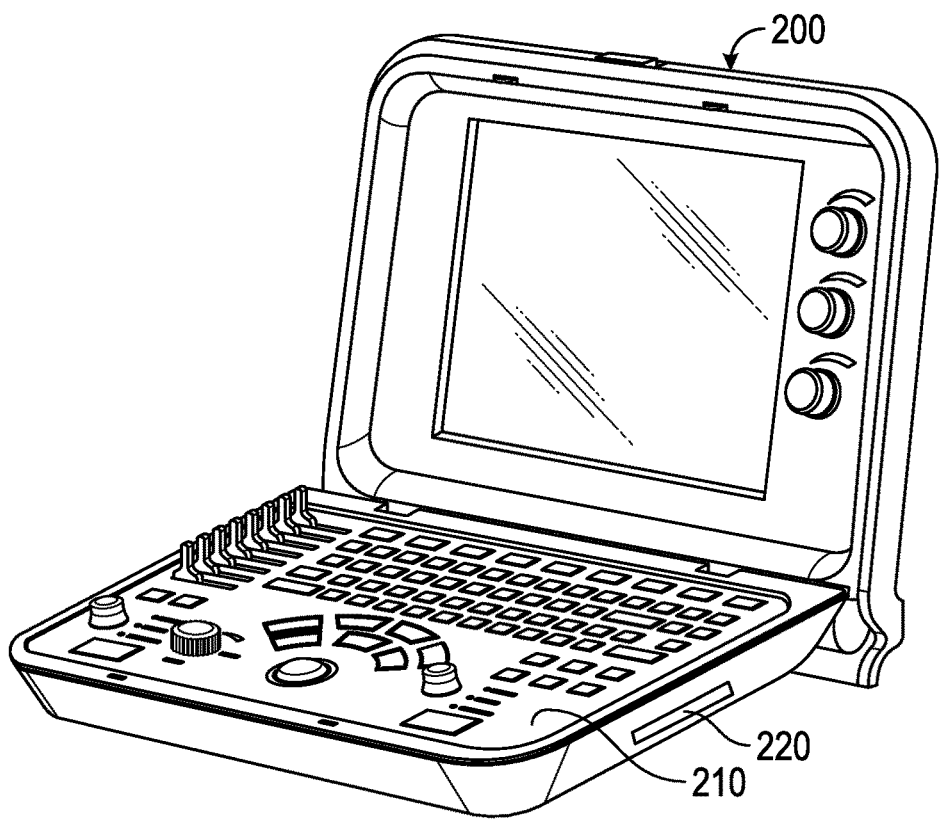
FIGS. 5-6 are elevation views of ultrasound equipment, according to an exemplary embodiment.
Figure 6:
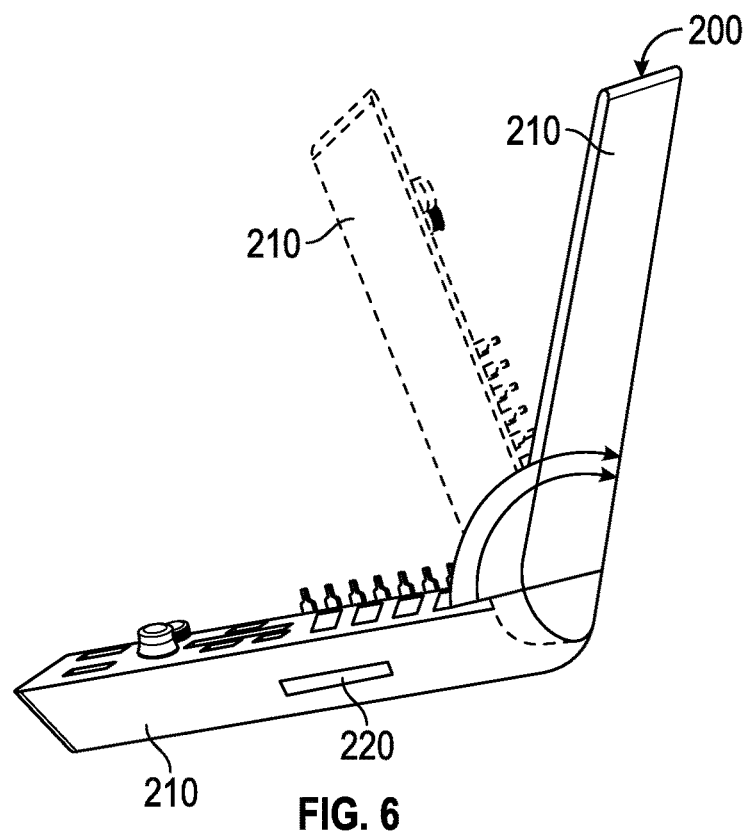
Figure 7:
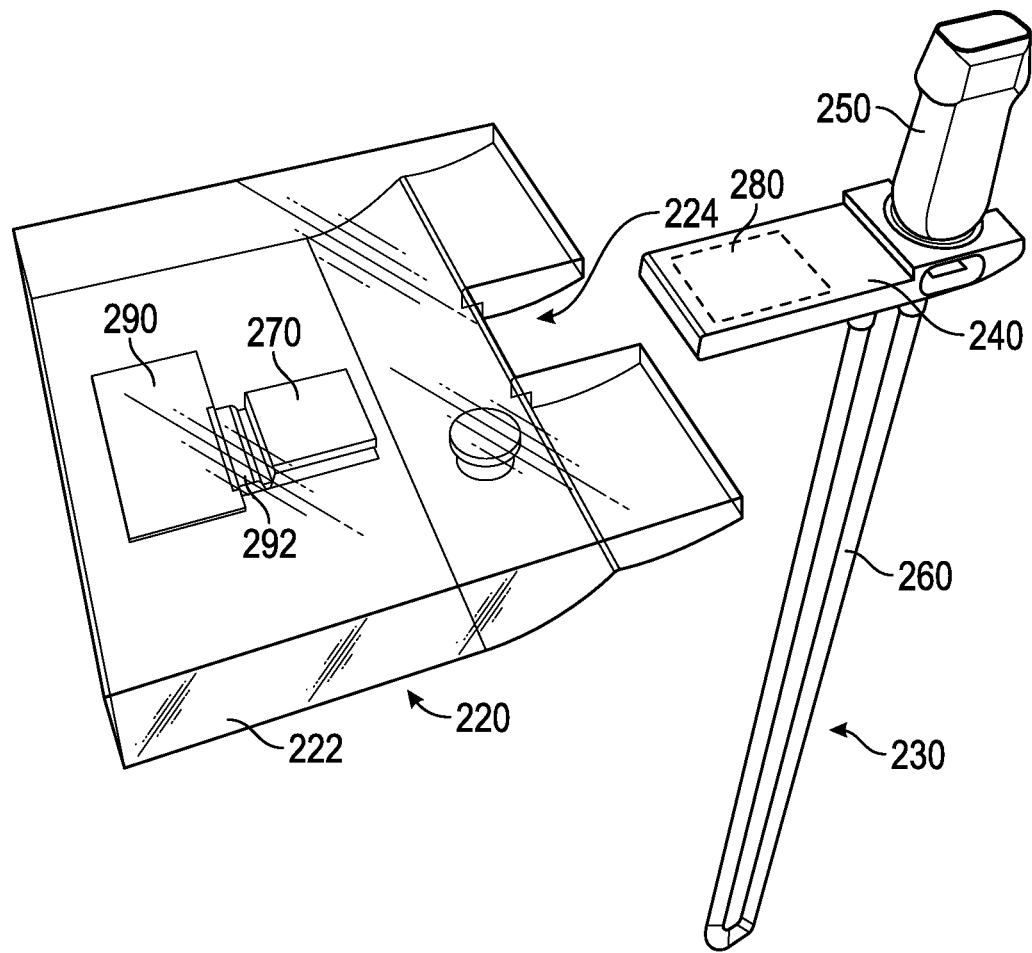
FIG. 7 is an elevation view of a receiver assembly of an ultrasound system and transducer assembly, according to an exemplary embodiment.

Referring generally to FIGS. 5-7, an ultrasound system of ultrasound equipment of the present disclosure is described. Ultrasound system 200 includes a body and a user interface, shown as control panel 210. According to an exemplary embodiment, a receiver assembly 220 is coupled to the housing of control panel 210. Receiver assembly 220 is configured to engage a transducer assembly 230, according to an exemplary embodiment. In one embodiment, receiver assembly 220 is integrally formed with the housing of ultrasound system 200. According to an alternative embodiment, receiver assembly 220 is removably coupled with ultrasound system 200 (i.e. receiver assembly 220 may itself be removed from ultrasound system 200). As shown in FIGS. 5-6, the ultrasound system's housing may take the shape of a laptop computer. In other embodiments, the ultrasound system can be formed as a tablet or another relatively thin housing. The cartridge and housing shape disclosed herein may advantageously facilitate the use of relatively small ultrasound system housings (e.g., laptop shaped, etc.).

As shown in FIGS. 5-6, receiver assembly 220 is positioned along control panel 210. Receiver assembly 220 may be coupled to the housing of control panel 210 at approximately the same vertical position as control panel 210 (i.e. within the user's normal work zone). According to an exemplary embodiment, receiver assembly 220 coupled to housing at approximately the same vertical position as control panel 210 reduces the need for a user to bend over to disconnect a transducer connector from ultrasound system 200, thereby improving the ergonomic performance of the ultrasound equipment. A user may interact with control panel 210 and position transducer probe 250 to perform a diagnostic ultrasound examination.

As shown in FIG. 7, receiver assembly 220 includes a body 222 having an opening, shown as slot 224, that receives transducer assembly 230. According to an exemplary embodiment, transducer assembly 230 includes an insert, shown as cartridge 240, coupled to a transducer probe 250 with a cable 260. Cartridge 240 may be positioned into slot 224 of body 222 to couple transducer assembly 230 with ultrasound system 200. Cartridge 240 is movable between a removed position with respect to slot 224, in which cartridge 240 is not received within slot 224, a partially inserted position, in which cartridge 240 is partially received within slot 224, and a fully engaged position, in which cartridge 240 is received in slot 224 in a manner that electrically couples transducer probe 250 to ultrasound system 200. Accordingly, transducer probe 250 may be electrically coupled with ultrasound system 200. As shown in FIG. 7, receiver assembly 220 includes a contact surface, shown as first connector half 270. First connector half 270 is moveably coupled to body 222 of receiver assembly 220. According to an alternative embodiment, first connector half 270 is fixed to body 222 of receiver assembly 220. As shown in FIG. 7, first connector half 270 is coupled to a processor, shown as circuit board 290, with a cable 292. Circuit board 290 interfaces with ultrasound system 200, according to an exemplary embodiment. Cartridge 240 also includes a contact surface, shown as second connector half 280. Second connector half 280 is electrically coupled to transducer probe 250 with cable 260. A first end of cable 260 is coupled to transducer probe 250, and a second end of cable 260 is fixed to cartridge 240. According to an exemplary embodiment, contact between first connector half 270 and second connector half 280 electrically couples transducer probe 250 with ultrasound system 200. The electrical coupling may occur when cartridge 240 is received in the fully engaged position within slot 224.

According to an exemplary embodiment, first connector half 270 and second connector half 280 include a plurality of flat conductive surfaces (e.g., a plurality of copper contacts). According to an alternative embodiment, the conductive surfaces are curved (e.g., bowed), deformation of the curved conductive surfaces maintaining engagement between first connector half 270 and second connector half 280. In such an arrangement, when the mating bowed conductive surfaces are deformed (i.e., when cartridge 240 is in the fully engaged position), the bowed surfaces form a friction fit or a snap fit connection such that a holding force is created that resists cartridge 240 removal from slot 224. According to still another alternative embodiment, first connector half 270 and second connector half 280 include a plurality of interengaging pins and recesses. In such an arrangement, when the interengaging pins and recesses are engaged (i.e., when cartridge 240 is in the fully engaged position), a holding force is created that resists cartridge 240 removal from slot 224. In still other embodiments, first connector half 270 otherwise interfaces with second connector half 280 to electrically couple transducer probe 250 with ultrasound system 200.

Figure 8:
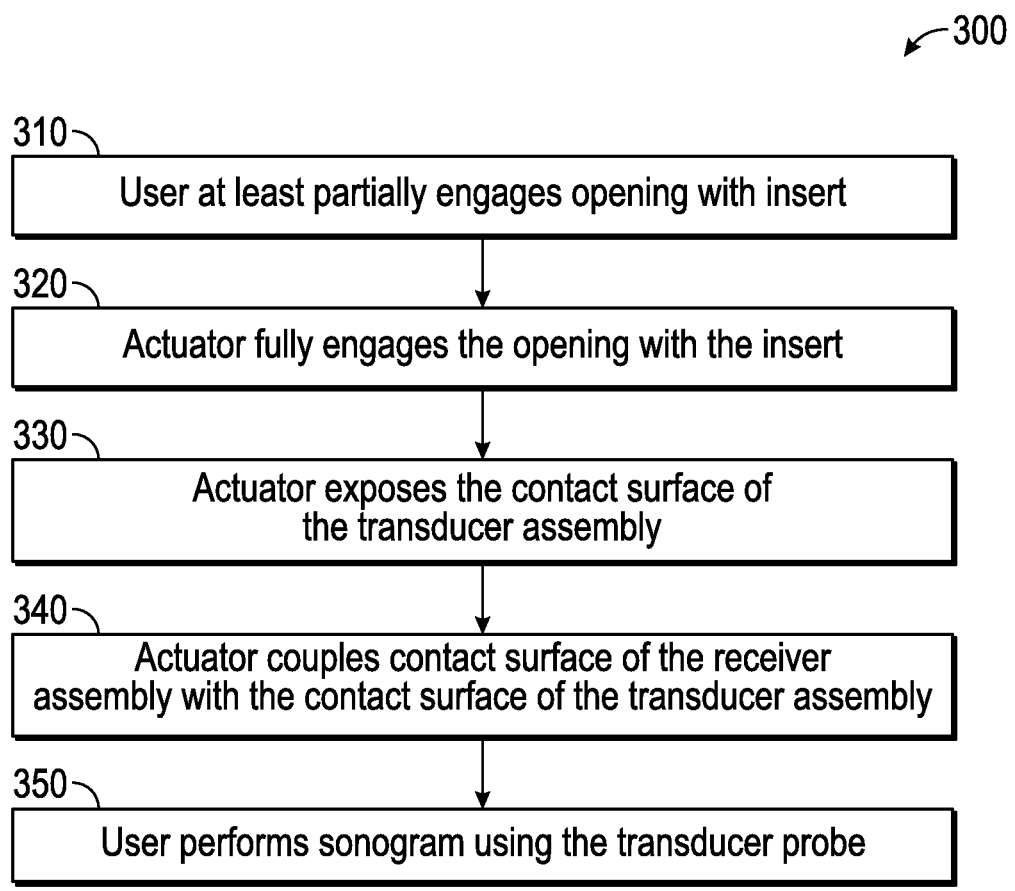
FIG. 8 is a flow chart of a method for a user engaging the transducer assembly with the ultrasound system and performing a diagnostic ultrasound examination, according to an exemplary embodiment.

Referring next to FIG. 8, a user may engage a transducer assembly (e.g., transducer assembly) with an ultrasound system (e.g., ultrasound system 200) and perform a diagnostic ultrasound examination according to method 300. A user first at least partially engages an opening of a receiver assembly with an insert of the transducer assembly (step 310). In some embodiments, the user fully engages the opening with the insert. According to the alternative embodiment shown in FIG. 8, the user partially engages the opening with the insert, and an actuator thereafter fully engages the opening with the insert (step 320). The actuator may include a rack and pinion gear mechanism, a linear actuator that pulls the insert into the opening, or still another device configured to fully engage the cartridge with the slot. According to an exemplary embodiment, the receiver assembly includes at least one of a switch and a sensor that detects the presence of the insert. A processing circuit may receive a signal from at least one of the switch and the sensor and send a signal to engage the actuator. The processing circuit may include a processor and a memory.

In the fully engaged position, a contact surface of the transducer assembly is disposed along (e.g., above, below, to a side of, etc.) a contact surface of the receiver assembly. An actuator exposes the contact surface of the transducer assembly (step 330). According to an exemplary embodiment, exposing the contact surface of the transducer assembly with the insert in the fully engaged position reduces the risk that debris may become disposed on the contact surface. With the insert in the fully engaged position, an actuator couples the contact surface of the receiver assembly with the contact surface of the transducer assembly (step 340). By way of example, the contact surface may be moveably coupled to the body of the receiver assembly, and a linear actuator may press the contact surface of the receiver assembly into engagement with the contact surface of the transducer assembly. Upon engagement between the contact surface of the receiver assembly and the contact surface of the transducer assembly, the transducer probe may be electrically coupled to the ultrasound system. A user may thereafter perform a sonogram using the transducer probe (step 350).

Figure 9:
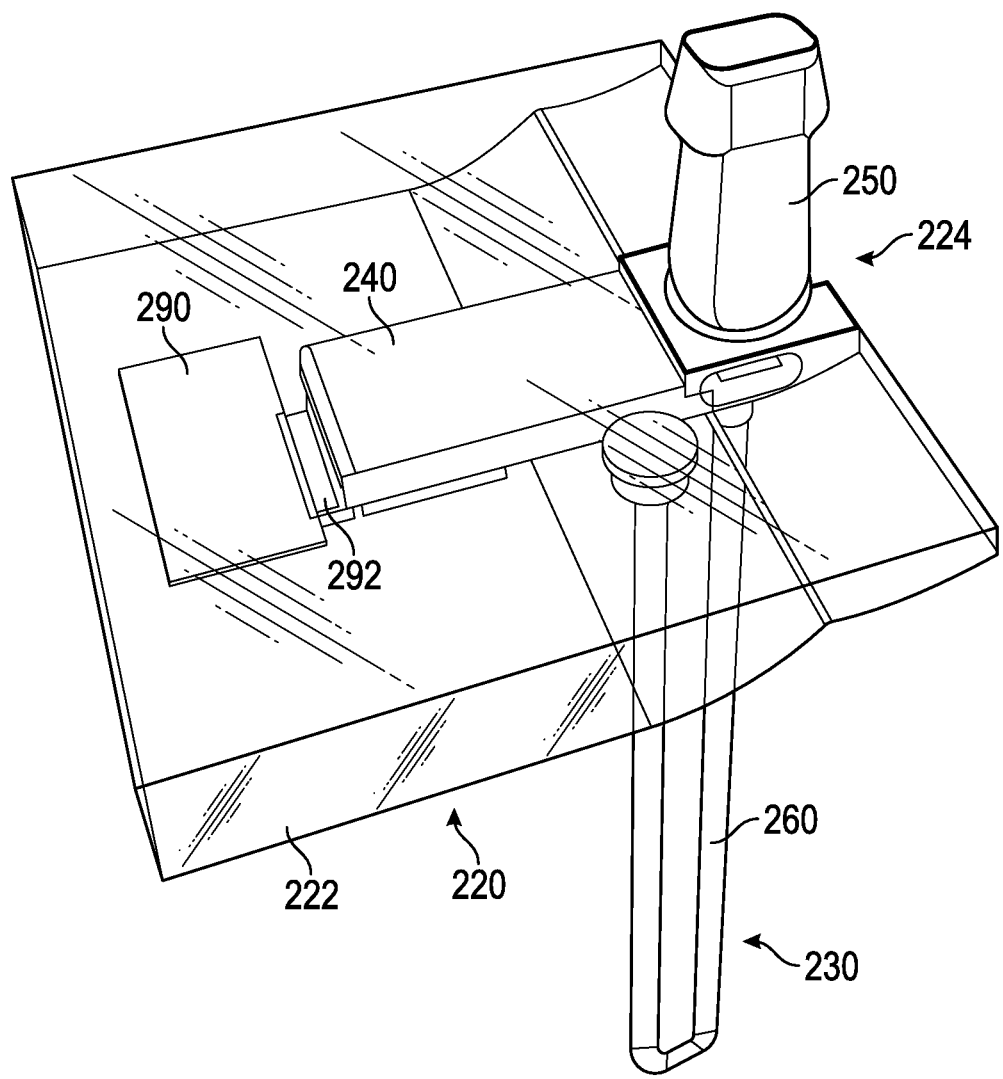
FIGS. 9-14 are detailed elevation views illustrating the transducer assembly engaging with the receive assembly of the ultrasound system, according to an exemplary embodiment.

Referring next to the exemplary embodiment shown in FIGS. 9-14, transducer assembly 230 may engage receiver assembly 220. As shown in FIG. 9, cartridge 240 of transducer assembly 230 is in a fully engaged positioned within slot 224 of body 222. According to an exemplary embodiment, a user fully positions cartridge 240 into slot 224. According to an alternative embodiment, an actuator at least partially positions cartridge 240 into slot 224. The actuator may include a pinion gear that engages a gear rack on cartridge 240. Rotation of the pinion gear may pull cartridge 240 into slot 224. According to an alternative embodiment, the actuator includes a linear actuator having an end that is releasably coupled to cartridge 240. The end may engage cartridge 240, and the linear actuator may pull cartridge 240 into slot 224. According to an exemplary embodiment, receiver assembly 220 includes at least one of a switch and a sensor (e.g., a proximity sensor, etc.) that detects the presence of cartridge 240 (e.g., at the outer end of body 222). A processing circuit may receive a signal from at least one of the switch and the sensor and send a signal to engage the actuator. The processing circuit may include a processor and a memory.

Figure 10:
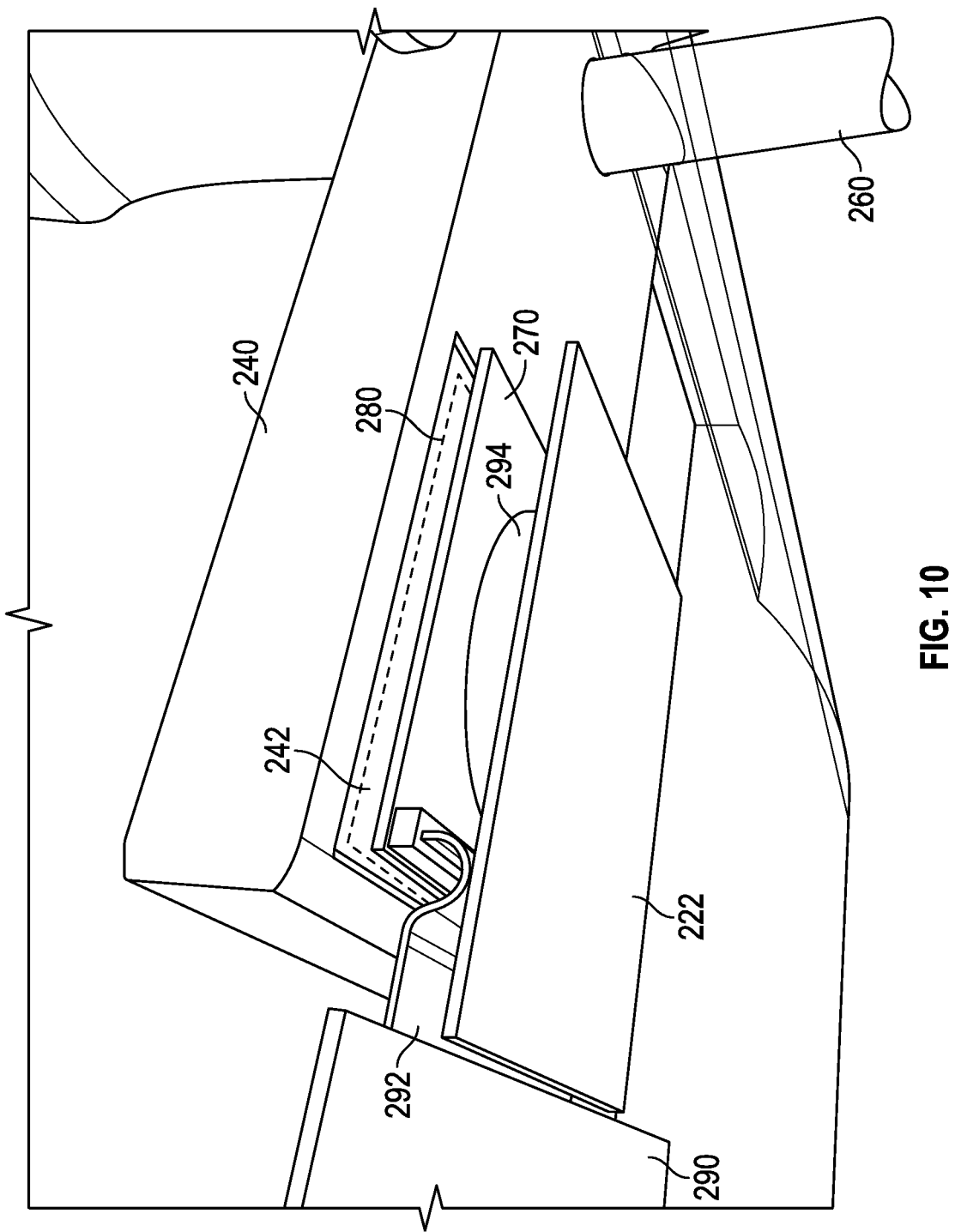
Figure 11:
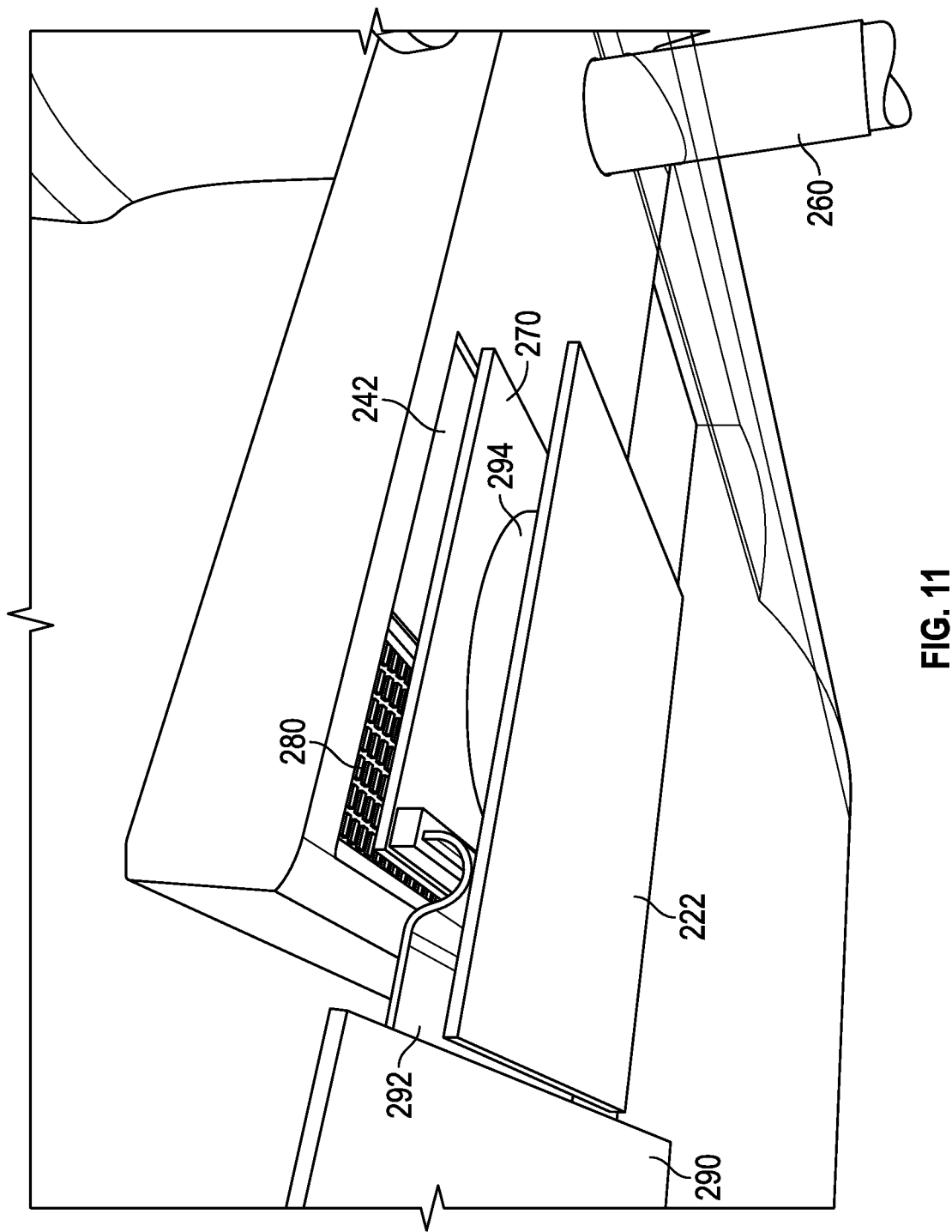

As shown in FIGS. 10-11, cartridge 240 includes a cover, shown as door 242, positioned over second connector half 280. Cover 240 may be coupled to cartridge 240. In some arrangements, cover 240 is slidably coupled to cartridge 240. In such an arrangement, cover 240 may be slid between a first position, in which connector half 280 is covered by cover 240, and a second position, in which connector half 280 is exposed. In the second position, cover 240 may be received within the body of cartridge 240. An actuator slides door 242 along cartridge 240 to expose second connector half 280, according to an exemplary embodiment. In other embodiments, door 242 otherwise moves relative to cartridge 240 thereby exposing second connector half 280. In one embodiment, the actuator is engaged (e.g., with a processing circuit) after cartridge 240 reaches the fully engaged position. At least one of a switch and a sensor may be positioned to detect the position of cartridge 240. In one embodiment, a proximity switch is coupled to an end of cartridge 240. As cartridge 240 is drawn into slot 224, the proximity switch approaches an end face of slot 224. Once cartridge 240 reaches the fully engaged position, the proximity switch may interrupt the circuit that engages the actuator configured to draw cartridge 240 into slot 224. According to an alternative embodiment, an interengaging tab system (e.g., a first tab coupled to door 242 and a second tab coupled to body 222) slides door 242 along cartridge 240. In one embodiment, an end face of cartridge 240 contacts an end face of slot 224 as cartridge 240 reaches the fully engaged position. According to an alternative embodiment, an end face of cartridge 240 is offset from an end face of slot 224 (e.g., 1.0 centimeters) in the fully engaged position.

The actuator slides door 242 along cartridge 240 as cartridge 240 reaches the fully engaged position. In other embodiments, the actuator begins to slide door 242 along cartridge 240 before cartridge reaches the fully engaged position. Engaging the actuator after cartridge 240 reaches the fully engaged position reduces the risk that debris may become disposed on second connector half 280. According to an alternative embodiment, cartridge 240 does not include door 242.

Figure 12:
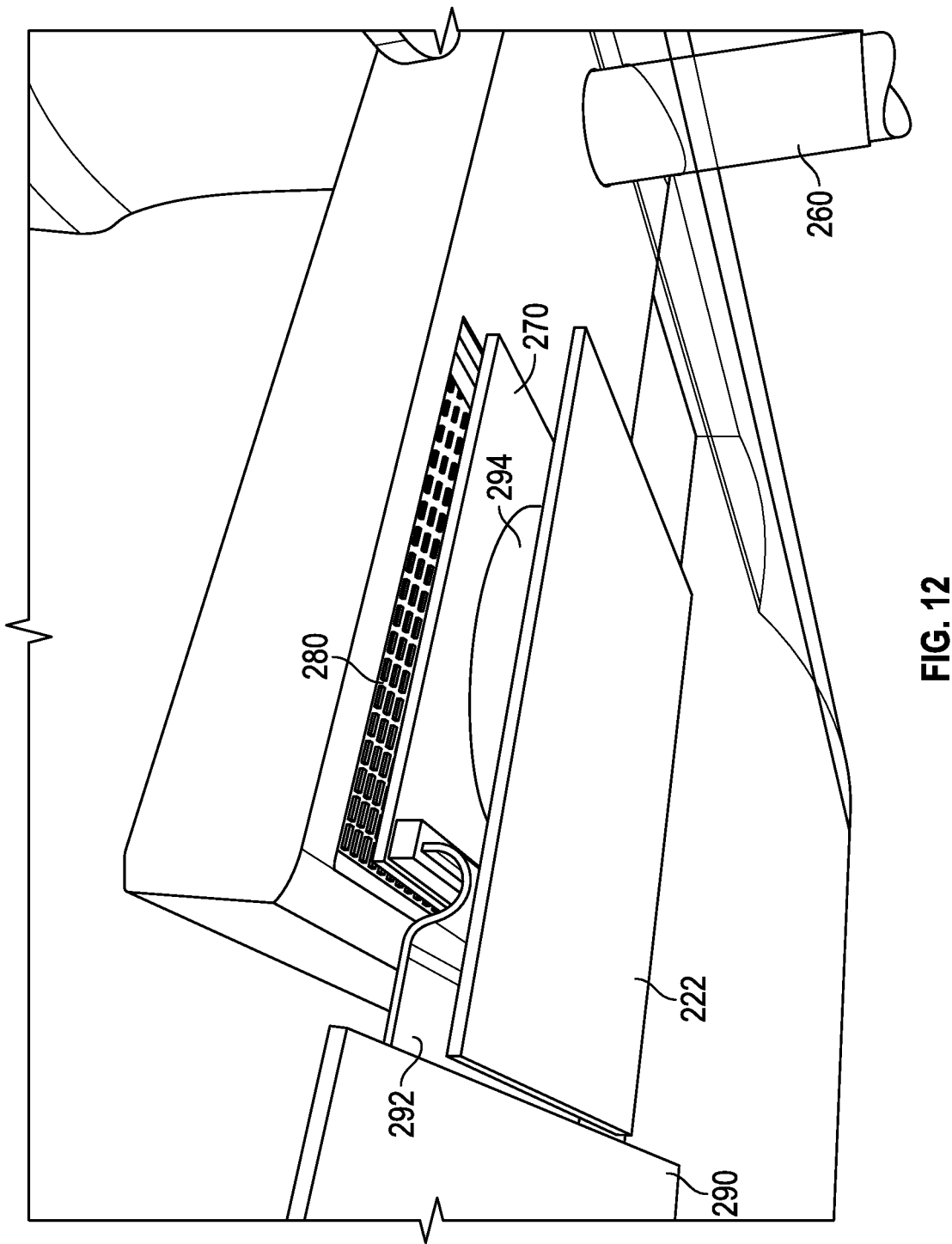
Figure 13:
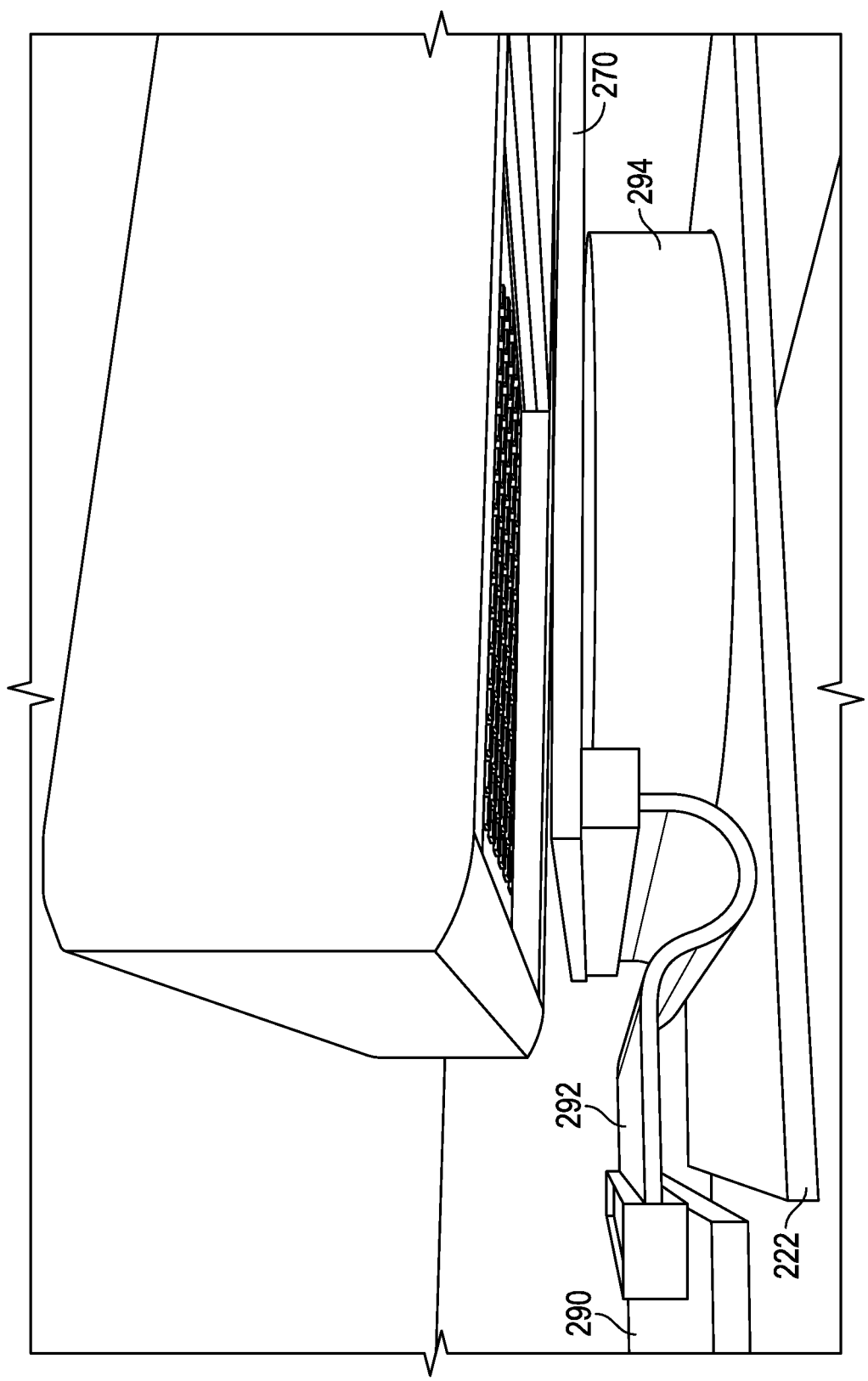
Figure 14:
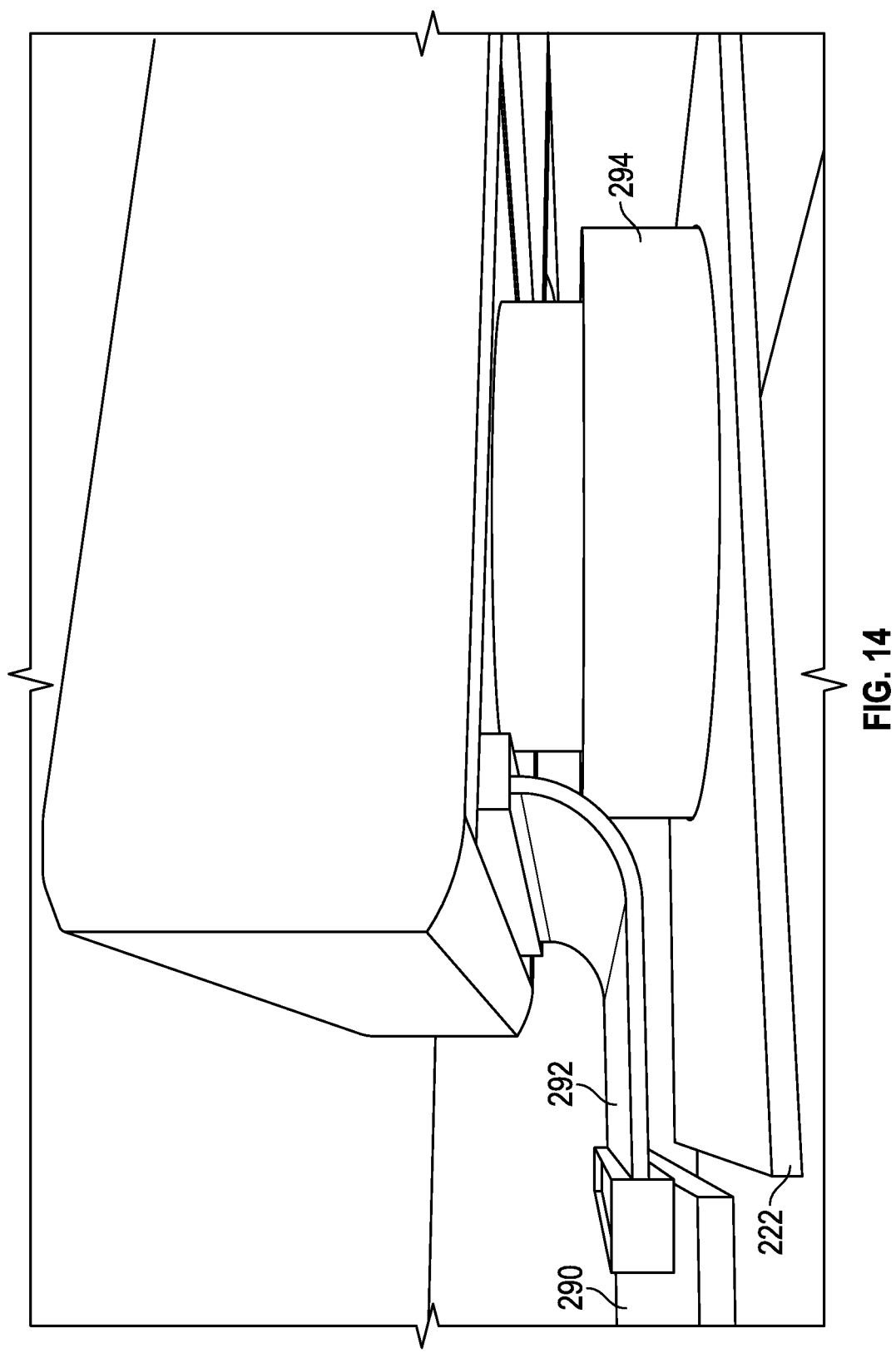

Referring next to FIGS. 12-14, receiver assembly 220 includes an actuator, shown as solenoid 294. As shown in FIGS. 12-14, solenoid 294 is disposed between body 222 and first connector half 270. According to an exemplary embodiment, as cartridge 240 reaches the fully engaged position, a processing circuit sends a signal to solenoid 294. Upon receiving the signal, solenoid 294 extends, thereby moving first connector half 270 into engagement with second connector half 280. Positioning at least one of cartridge 240 and first connector half 270 with an actuator reduces the need for a user to perform precise hand movements involved with locking or unlocking connectors from a lower portion of ultrasound equipment. The actuators also reduce the need for a user to apply force to engage the first connector half 270 and the second connector half 280.

As shown in FIG. 14, cable 292 includes a slack length that facilitates movement of first connector half 270 upward and into engagement with second connector half 280. According to an exemplary embodiment, first connector half 270 enters cartridge 240 as it engages second connector half 280 to form an electrical connection. As shown in FIG. 14, the electrical connection is positioned within cartridge 240, thereby reducing the risk that debris may interfere with the electrical connection and interrupt the operation of the ultrasound equipment.

According to an alternative embodiment, receiver assembly 220 does not include an actuator 294. In one embodiment, first connector half 270 engages second connector half 280 as door 242 slides along cartridge 240. In another embodiment, cartridge 240 does not include door 242, and first connector half 270 engages second connector half 280 as cartridge 240 reaches the fully engaged position.

As shown in FIGS. 7 and 9-14, second connector half 280 is positioned along a lower surface of cartridge 240. According to an alternative embodiment, second connector half 280 is positioned along an upper or side surface of cartridge 240. According to still another alternative embodiment, second connector half is positioned at least partially with cartridge 240 (e.g., a cylinder extending along a middle portion of cartridge 240). First connector half 270 may be shaped and positioned to interface with second connector half 280 with cartridge 240 in the fully engaged position.

According to an exemplary embodiment, cartridge 240 includes a holder portion, shown as retaining portion 244. When not in use, transducer probe 250 may be engaged with (e.g., interlock, rest upon, etc.) retaining portion 244. Cartridge 240 having retaining portion 244 reduces the need for a user to hold the transducer connector in one hand and transducer probe 250 in another hand when moving transducer assembly 230. According to an exemplary embodiment, a user may move transducer assembly 230 from a first receiver assembly 220 to a second receiver assembly 220 with one hand. Retaining portion 244 may have a shape that corresponds with the shape of transducer probe 250. In some embodiments, different cartridges 240 and transducer probes 250 may be engaged with receiver assembly 220. Each of the different cartridges 240 may include a retaining portion 244 that is shaped to correspond with the particular transducer probe 250.

Figure 15:
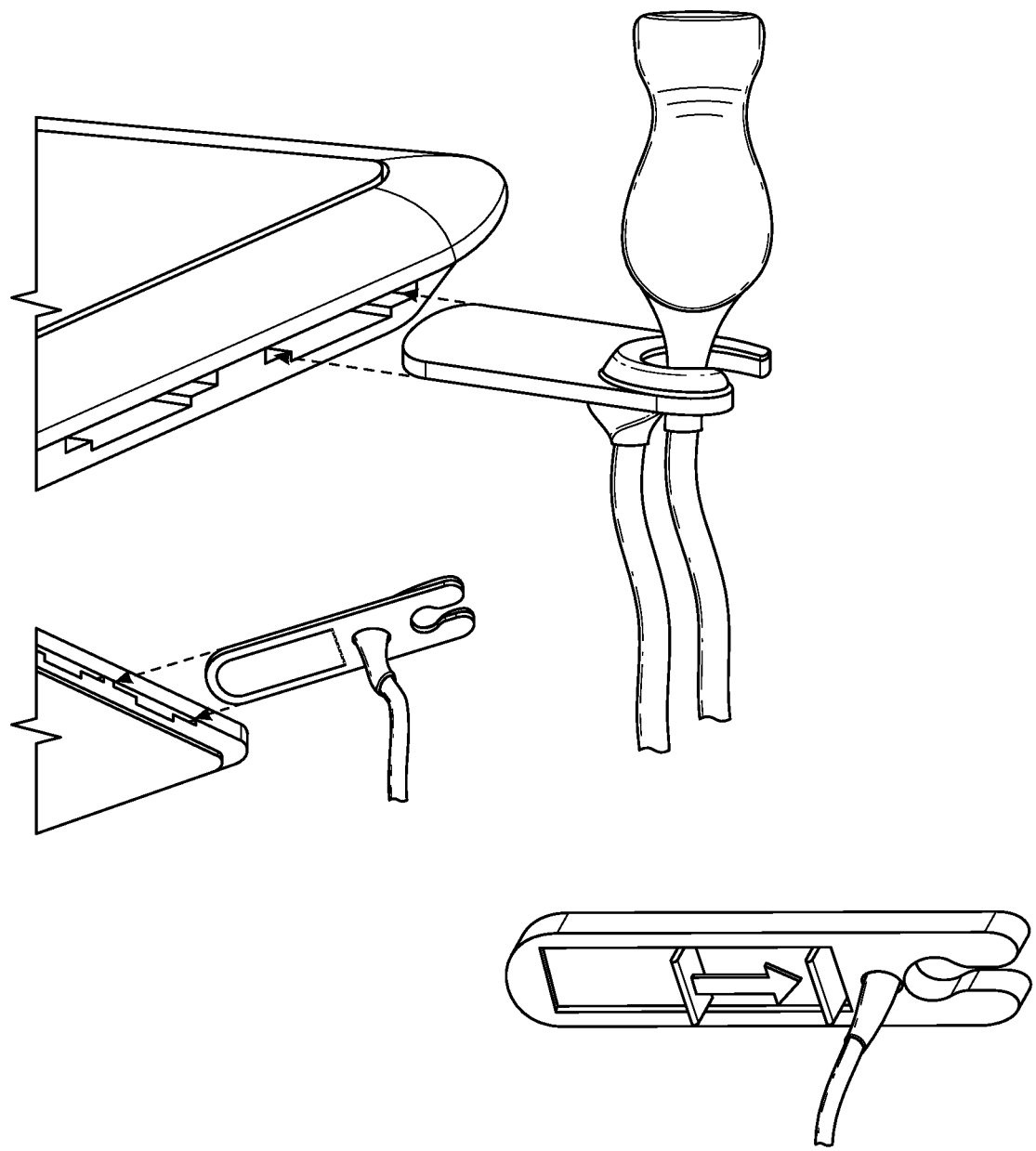
FIGS. 15, 16, and 17A-17C are additional views of the ultrasound system of the present disclosure, according to an exemplary embodiment.
Figure 16:
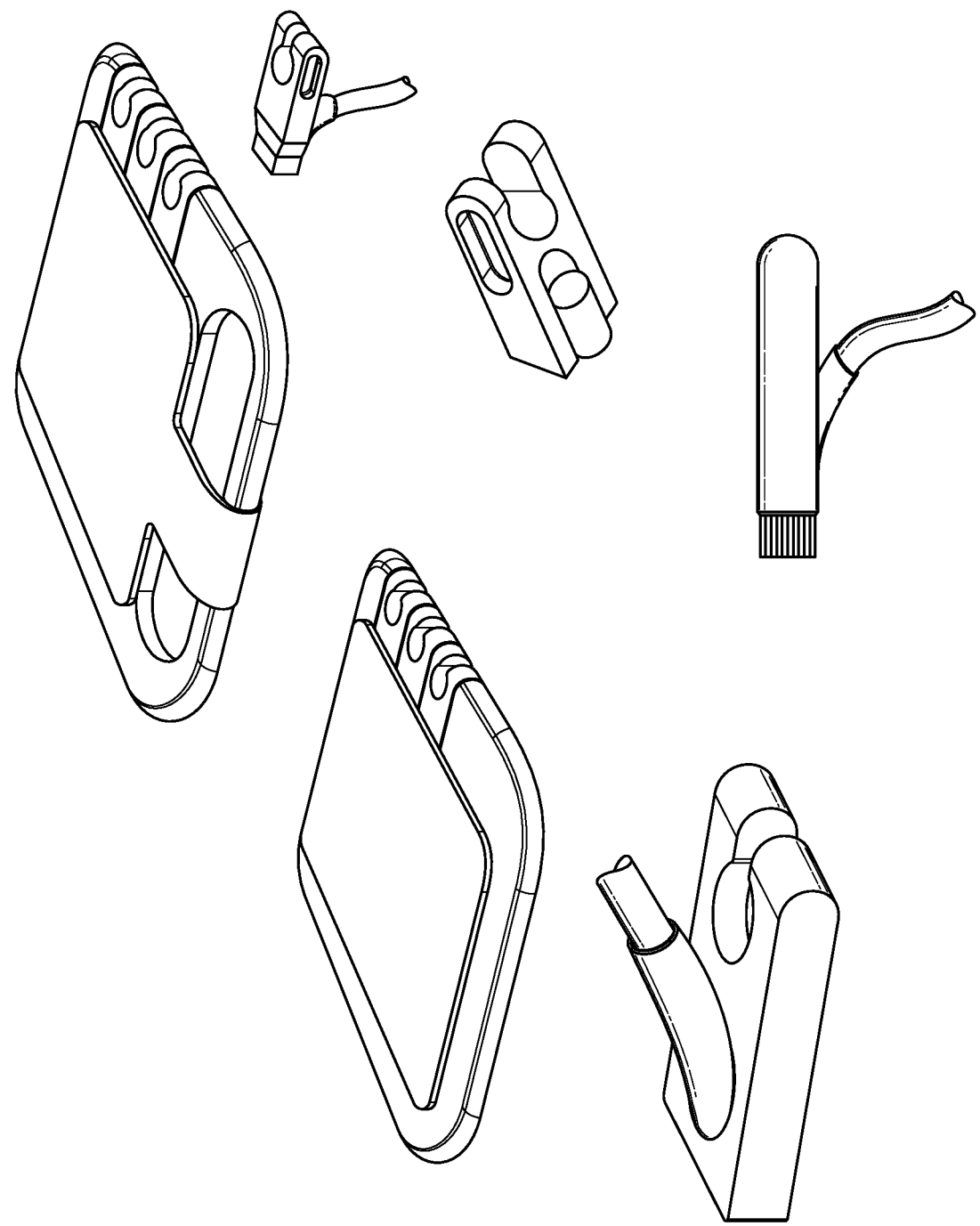

FIG. 15-17 are additional views of the ultrasound system of the present disclosure, according to an exemplary embodiment.

In FIG. 15, the cartridge is shown as a blade connector which can hold the transducer. As is shown, extra material may extend above the claw which holds the transducer head. The extra material may be a soft material with a higher degree of elasticity than hard plastic. As shown, the underside of the connector blade can include an interface for the cord or cable. The interface for the cord or cable can have a strain relief as shown in FIG. 15. As shown, the ultrasound machine may include a plurality of slots for receiving a plurality of blade shaped transducer connector cartridges. FIG. 15 further illustrates one embodiment of an underside for the blade connector. The blade connector can include a door which automatically slides open via interaction between the housing of the ultrasound machine and the door lip when the blade connector is inserted. In this embodiment, the door may be spring biased to a shut position. In other embodiments the door is not biased at all. In yet other embodiments the door is based against movement, requiring some force to move the door between open and closed (and then open again) positions. Opening the door can expose a micro-pinless connector. In other embodiments, the blade connector may carry one or more connector pins within the door.

In FIG. 16, alternative embodiments for the ultrasound machine are shown. The ultrasound machines of FIG. 16 include three blade connectors installed side by side. In these embodiments, the blade connectors are thick enough such that they sit flush with the surfaces of the housing of the ultrasound machine when fully seated. As shown, each blade connector may include depressions on the side to facilitate gripping by the user and/or by the ultrasound machine's connection mechanism. A strain relief for the cord may be diagonally oriented to facilitate laptop computing (getting the cord out of the way of a user's legs).

Figure 17A:
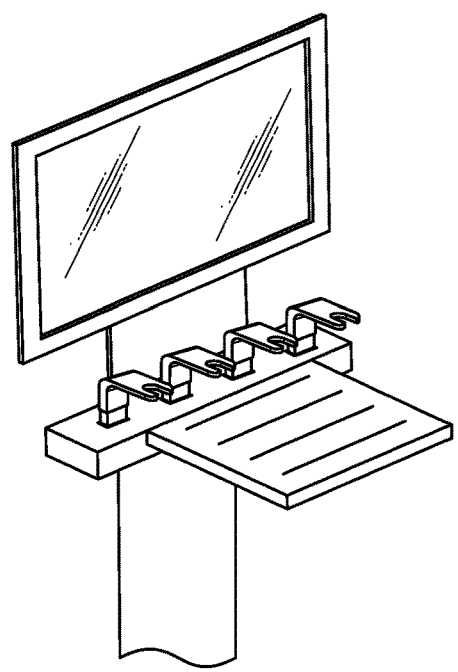
Figure 17B:
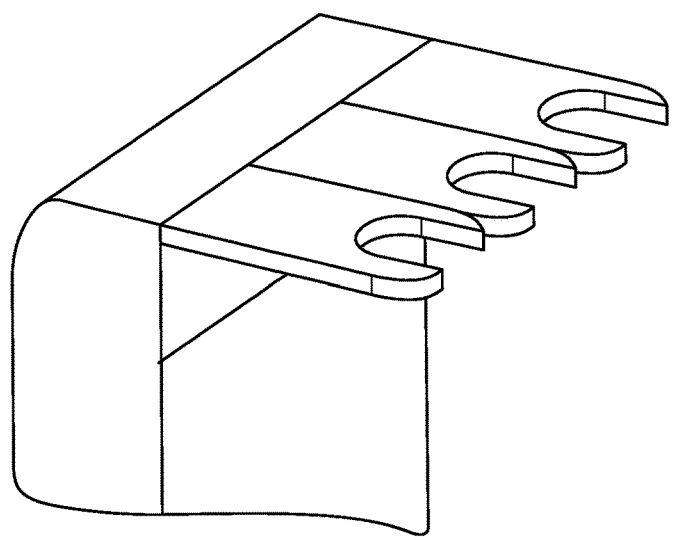
Figure 17C:
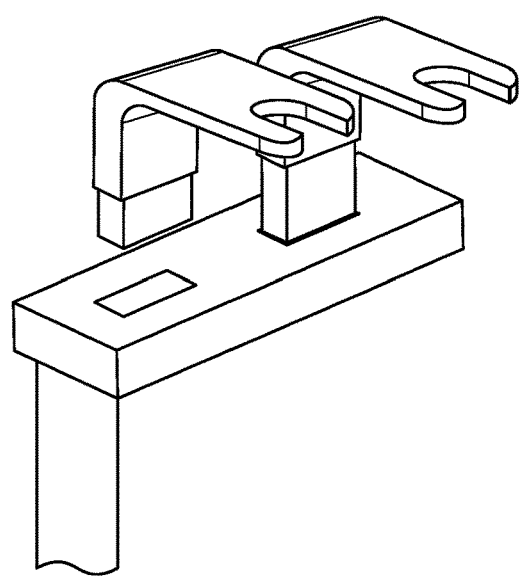

In FIGS. 17A-C, additional embodiments are shown in which the ultrasound machine does not take the form of a laptop, tablet or other portable unit. In these embodiments, the ultrasound machine is a station. In some embodiments, e.g., FIG. 17B, the same blade connectors as are utilized on the portable ultrasound machines may be utilized. In other embodiments (e.g., 17A, 17C), the ultrasound station may use bent connector blades to facilitate gravity aided stabilizing and seating, while maintaining a hook eye which is parallel to the ground.

In various exemplary embodiments contained herein, the connector blades or cartridges can house passive or active electronic circuits for affecting the performance of the connected transducers. For example, in some embodiments the transducers may include filtering circuitry, processing circuitry, amplifiers, transformers, capacitors, batteries, failsafe circuits, or other electronics which can customize or facilitate the performance of the transducer and/or the overall ultrasound machine.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It should be noted that the orientation of various elements may differ according to other exemplary embodiments, and that such variations are intended to be encompassed by the present disclosure.

It is important to note that the construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the enclosure may be constructed from any of a wide variety of materials that provide sufficient strength or durability, in any of a wide variety of colors, textures, and combinations. Additionally, in the subject description, the word "exemplary" may be used to mean serving as an example, instance or illustration. Any embodiment or design described herein as "exemplary" may be not necessarily to be construed as preferred or advantageous over other embodiments or designs. Rather, use of the word exemplary may be intended to present concepts in a concrete manner. Accordingly, all such modifications are intended to be included within the scope of the present inventions. The order or sequence of any process or method steps may be varied or re-sequenced according to alternative embodiments. Any means-plus-function clause may be intended to cover the structures described herein as performing the recited function and not only structural equivalents but also equivalent structures. Other substitutions, modifications, changes, and omissions may be made in the design, operating conditions, and arrangement of the preferred and other exemplary embodiments without departing from scope of the present disclosure or from the spirit of the appended claims.

What is claimed is:

1. An ultrasound transducer assembly comprising:
    a cartridge configured to be received in a slot of an ultrasound device;
    an ultrasound probe coupled to the cartridge via a cable extending from the ultrasound probe to an interface of the cartridge;
    the cartridge including a retaining portion configured to hold the ultrasound probe, the retaining portion including a recess configured to receive the ultrasound probe and the cable into the retaining portion; and
    a first contact surface coupled to the cartridge, wherein the first contact surface is configured to contact a second contact surface of the ultrasound device when the cartridge is positioned within the slot to electrically couple the ultrasound probe to the ultrasound device.

2. The ultrasound transducer assembly of claim 1, wherein the retaining portion includes a shape that corresponds with a shape of the ultrasound probe.

3. The ultrasound transducer assembly of claim 2, wherein the recess defines a length that is less than an outer length of the ultrasound probe.

4. The ultrasound transducer assembly of claim 1, wherein the retaining portion is positioned on an opposite side of the cartridge from the first contact surface such that the retaining portion and the ultrasound probe are positioned outside of the slot when the cartridge is received in the slot.

5. The ultrasound transducer assembly of claim 1, wherein the cartridge includes a blade shape.

6. The ultrasound transducer assembly of claim 5, wherein the retaining portion extends away from a first outer surface of the cartridge.

7. The ultrasound transducer assembly of claim 1, wherein the interface for the cable is positioned adjacent to the first contact surface.

8. The ultrasound transducer assembly of claim 1, wherein holding the ultrasound probe with the retaining portion allows a user to move the cartridge and the ultrasound probe together with one hand.

9. An ultrasound system comprising:
an ultrasound device including a housing, a control panel coupled to the housing, and a receiver assembly coupled to the housing, wherein the receiver assembly includes a first contact surface; and
a transducer assembly including:
a cartridge configured to be received in the receiver assembly of the ultrasound device;
an ultrasound probe coupled to the cartridge via a cable extending from the ultrasound probe to an interface of the cartridge;
the cartridge including a retaining portion configured to hold the ultrasound probe, the retaining portion including a recess configured to receive the ultrasound probe and the cable into the retaining portion; and
a second contact surface coupled to the cartridge, wherein the second contact surface is configured to contact the first contact surface of the ultrasound device when the cartridge is positioned within the receiver assembly to electrically couple the ultrasound probe to the ultrasound device.

10. The ultrasound system of claim 9, wherein the retaining portion includes a shape that corresponds with a shape of the ultrasound probe.

11. The ultrasound system of claim 9, wherein the retaining portion is positioned on an opposite side of the cartridge from the second contact surface such that the retaining portion and the ultrasound probe are positioned outside of the receiver assembly when the cartridge is received in the receiver assembly.

12. The ultrasound system of claim 9, wherein the cartridge includes a blade shape.

13. The ultrasound system of claim 12, wherein the retaining portion extends away from a first outer surface of the cartridge.

14. The ultrasound system of claim 9, wherein the interface for the cable is positioned adjacent to the first contact surface.

15. The ultrasound system of claim 9, further comprising a cover slidably coupled to the cartridge, the cover configured to slide between a first position in which the second contact surface is covered and a second position in which the second contact surface is exposed.

* * * * *